United States Patent [19]
Kropp et al.

[11] Patent Number: 6,069,281
[45] Date of Patent: May 30, 2000

[54] PROCESS FOR PRODUCING ORGANIC NITROGEN COMPOUNDS, SPECIAL ORGANIC NITROGEN COMPOUNDS AND MIXTURES OF SUCH COMPOUNDS AND THEIR USE AS FUEL AND LUBRICANT ADDITIVES

[75] Inventors: Rudolf Kropp; Wolfgang Siegel; Boris Breitscheidel, all of Limburgerhof; Wolfgang Harder, Weinheim; Harald Schwahn, Wiesloch; Wolfgang Reif, Frankenthal, all of Germany

[73] Assignee: BASF Aktiengesellschaft, Ludwigshafen, Germany

[21] Appl. No.: 08/983,232

[22] PCT Filed: Jul. 4, 1996

[86] PCT No.: PCT/EP96/02928

§ 371 Date: Jan. 13, 1998

§ 102(e) Date: Jan. 13, 1998

[87] PCT Pub. No.: WO97/03946

PCT Pub. Date: Feb. 6, 1997

[30] Foreign Application Priority Data

Jul. 17, 1995 [DE] Germany .................. 195 25 938

[51] Int. Cl.[7] ................................. C07C 209/00
[52] U.S. Cl. ................ 564/494; 564/495; 508/549; 44/414
[58] Field of Search ................ 564/494, 495

[56] References Cited

U.S. PATENT DOCUMENTS

| | | | |
|---|---|---|---|
| 2,478,243 | 8/1949 | Coe et al. ............... | 260/644 |
| 3,438,757 | 4/1969 | Honnen et al. ........... | 44/58 |
| 3,485,875 | 12/1969 | Menapace ............... | 564/494 |
| 3,594,419 | 7/1971 | Rosenthal ............... | 564/494 |
| 3,681,463 | 8/1972 | Lee ........................ | 564/495 |
| 3,766,271 | 10/1973 | Knifton ................. | 564/494 |
| 3,917,705 | 11/1975 | Swanson et al. ......... | 564/494 |
| 3,917,706 | 11/1975 | Hudson, Jr. et al. ...... | 564/494 |
| 5,103,061 | 4/1992 | Blackborow et al. ...... | 564/472 |
| 5,879,420 | 3/1999 | Kropp et al. ............. | 564/495 |

FOREIGN PATENT DOCUMENTS

| | | |
|---|---|---|
| 384 086 | 8/1990 | European Pat. Off. . |
| 606 976 | 7/1994 | European Pat. Off. . |
| 1172818 | 12/1969 | United Kingdom . |
| 96/03367 | 2/1996 | WIPO . |

OTHER PUBLICATIONS

Database Crossfire, XP002017950 (Centralblatt, 1913, p. 1376).
Database Crossfire, XP002017951 (J. Chem. Soc., 1955, pp. 1547, 1551).
Database Crossfire, XP002017952 (Pol. J. Chem., vol. 60, No. 4–6, 1986, pp. 625–630).
Database Crossfire, XP002017953 (J. Sci., vol. 30, 1926, p. 206).
Database Crossfire, XP002017954 (Heterocycles, vol. 36, No. 8, 1993, pp. 1823–1836).
Database Crossfire, XP002017955 (Hel. Chim. Acta, vol. 11, 1928, pp. 694, 695.
Database Crossifre, XP002017956 (J. Chem. Soc., vol. 85, 1904, p. 832).
Database Crossfire, XP002017957 (C.R. Hebc. Seances Acad. Sci., vol. 224, 1947, pp. 1116, 1117).

*Primary Examiner*—Ellen M. McAvoy
*Attorney, Agent, or Firm*—Keil & Weinkauf

[57] ABSTRACT

The invention relates to the preparation of organic nitrogen compounds, in particular of aminoalkanes, alkyloximes, alkylnitrones or mixtures thereof, which have only one nitrogen-functional group and no alcoholic hydroxyl groups in the molecule, from nitro-containing reaction products of polymers of $C_2$–$C_6$-olefins with an average degree of polymerization P=5–100 with nitrogen oxides or mixtures of nitrogen oxides and oxygen by hydrogenation of these reaction products. The invention also relates to particular mixtures of such aminoalkanes, alkyloximes and/or alkylnitrones and to individual compounds of these types themselves. The designated products are suitable as additives to fuels and lubricants.

16 Claims, No Drawings

PROCESS FOR PRODUCING ORGANIC NITROGEN COMPOUNDS, SPECIAL ORGANIC NITROGEN COMPOUNDS AND MIXTURES OF SUCH COMPOUNDS AND THEIR USE AS FUEL AND LUBRICANT ADDITIVES

The present invention relates to a process for preparing organic nitrogen compounds, in particular aminoalkanes, alkyloximes, alkylnitrones or mixtures thereof, from nitro-containing reaction products of olefin polymers with nitrogen oxides. The invention furthermore relates to specific organic nitrogen compounds and mixtures of such compounds, and to the use thereof as fuel and lubricant additives and to fuels for otto engines and lubricants containing these compounds or mixtures.

Carburetors and inlet systems for Otto engines, as well as injection systems for fuel metering in otto and diesel engines, are contaminated with impurities caused by dust particles from the air, uncombusted hydrocarbon residues from the combustion chamber and the crankshaft housing ventilation gases passed into the carburetor.

The residues shift the air/fuel ratio when idling and in the lower partial load range so that the mixture becomes richer, combustion becomes less complete and, in turn, the contents of uncombusted or partially combusted hydrocarbons in the exhaust gas become larger and the gasoline consumption increases.

It is known that, to avoid these disadvantages, fuel additives are used for keeping valves and carburetors or injection systems clean (M. Rossenbeck in Katalysatoren, Tenside, Mineralöl-additive, Editors J. Falbe, U. Hasserodt, pages 233 et seq., G. Thieme Verlag, Stuttgart, 1978).

At present two generations of such detergent additives are distinguished depending on the mode of action but also depending on the preferred site of action of auxiliaries of this type.

The first generation of additives was able only to prevent the formation of deposits in the intake system but not to remove deposits already present, whereas the additives of the second generation are able to do both ("keep-clean" and "clean-up" effects) in particular because of their excellent thermal stability, in particular also at zones of higher temperatures, namely at the inlet valves.

The principle of the molecular structure of fuel detergents can be stated in general to be the linkage of polar structures to usually high molecular weight, nonpolar or lipophilic residues.

Representatives of the second generation of additives are frequently products based on polyisobutenes in the nonpolar part of the molecule. Among these again additives of the polyisobutylamine type should be particularly emphasized.

Reaction products of higher olefins such as polyisobutenes or oligopropenes with nitrogen oxides and the use thereof as additives for mineral oil products are disclosed in German Patent Applications P 44 25 834.8 (1) and P 44 25 835.6 (2). Some aminoalkanes which may be derived from such nitro-containing reaction products, and ways for preparing them, are also described therein.

U.S. Pat. No. 3,681,463 (3) describes the preparation of oil-soluble aminoalkyl alcohols based on polypropene and polybutene with predominantly non-α double bonds by nitration of the underlying olefins with nitrogen tetroxide to give the corresponding nitro nitrate esters and reduction of these nitro nitrate esters with hydrogen in the presence of a metallic hydrogenation catalyst. The aminoalkyl alcohols obtained in this way are suitable as additives for mineral oil products.

FR-A 2 687 159 (4) discloses that nitrogen-containing polybutenes which are suitable as fuel or lubricant additives can be obtained by reacting polybutenes with aqueous nitric acid and subsequently treated with bases to form polybutene derivatives with reactive carbonyl groups and further reacting these polybutene derivatives with amines and subsequently hydrogenating.

The effect of the nitrogen-containing polyolefin derivatives disclosed in the prior art as additives for mineral oil products is still in need of improvement. It is an object of the present invention to provide fuel and lubricant additives with an improved effect. It was moreover the intention that it be possible to prepare such additives in good yields and high purities by simple and economic processes.

We have found that this object is achieved by a process for preparing organic nitrogen compounds, in particular aminoalkanes, alkyloximes, alkylnitrones or mixtures thereof, which have only one nitrogen-functional group and no alcoholic hydroxyl groups in the molecule, from nitro-containing reaction products of polymers of $C_2$–$C_6$-olefins with an average degree of polymerization $P=5$–$100$ with nitrogen oxides or mixtures of nitrogen oxides and oxygen, wherein the nitro-containing reaction products are hydrogenated directly after their formation from the olefin polymers and nitrogen oxides.

However, said aminoalkanes, alkyloximes and/or alkylnitrones can be prepared not only by direct hydrogenation of the nitro-containing reaction products. It is also possible for the purpose of the present invention to convert the nitro-containing reaction products, after their formation, by elimination with bases into nitro-containing alkenes and then to hydrogenate these, with the resulting aminoalkanes always being in the form of mixtures of compounds which differ in the number of carbon atoms.

Typical structural elements for nitro-containing alkenes of this type are the following:

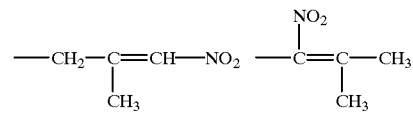

which are, for example, originally produced from a polyisobutene with terminal double bond (on the left) or from a polyisobutene with β double bond (on the right). Hydroxyl-containing compounds may also be byproducts of such antecedent elimination reactions. The product of the elimination reaction is, as a rule, a mixture of various species in which compounds with the structural element shown on the left above form the main component and compounds with the structural element shown on the right above occur only in small amounts or not at all.

Elimination reactions of this type are carried out under conditions customary for this purpose. Examples of bases which are employed are alkali metal hydroxides such as NaOH or KOH, alkali metal alcoholates such as sodium methanolate, sodium ethanolate, sodium isopropoxide or potassium tert-butoxide or, in particular, alkali metal carbonates or bicarbonates such as sodium or potassium carbonate or sodium or potassium bicarbonate. Also suitable as bases under special conditions for the elimination reactions are ammonia, amines in general, alkali metal fluorides or heterogeneous base systems such as basic ion exchangers.

In another embodiment of the present invention, the nitro-containing reaction products can, before the hydrogenation, be converted into compounds with reactive carbonyl groups and these can be reacted with ammonia or primary amines to give imines. In this case, the reactive carbonyl compound intermediate can be isolated or reacted directly in situ with the NH$_2$ group of the added amine to give the corresponding imine. It is possible in this case for the resulting organic nitrogen compounds derived from the primary amines employed also to have several nitrogen-functional groups and alcoholic hydroxyl groups in the molecule.

A typical reaction sequence of this type can be depicted as follows:

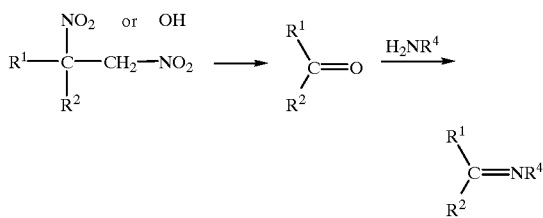

Examples of suitable primary amines for this imine formation are $C_1$–$C_{30}$-alkylamines or $C_3$–$C_{30}$-alkenylamines in which the alk(en)yl radicals can be interrupted by non-adjacent oxygen atoms or by NR$^2$ groups, where R$^2$ is hydrogen or $C_1$–$C_3$-alkyl, or can carry hydroxyl groups, or $C_5$–$C_8$-cycloalkylamines, $C_7$–$C_{18}$-aralkylamines, unsubstituted or substituted $C_6$–$C_{14}$-arylamines, diamines or polyamines of the general formula H$_2$N—(A—NR$^7$)$_m$—R$^8$, alkanolamines of the general formula H$_2$N—A—OH, ether amines, oligo- and polyether amines of the general formula H$_2$N—(A—O)$_m$—R$^7$ or oligo- and polyether alkanolamines of the general formula H$_2$N—(A—O)$_m$—A—OH, where A is $C_2$–$C_{10}$-alkylene, $C_5$–$C_{18}$-cycloalkylene or phenylene, R$^7$ and R$^8$ are hydrogen or $C_1$–$C_8$-alkyl and m is a number from 1 to 8. Typical individual examples of such primary amines are methylamine, ethylamine, n-propylamine, isopropylamine, n-butylamine, isobutylamine, tert-butylamine, 2-ethylhexylamine, stearylamine, oleylamine, allylamine, cyclohexylamine, benzylamine, aniline, toluidines, 1,2-diethylenediamine, 1,3-dipropylenediamine, 3-(N,N-dimethylamino)propylamine, diethylenetriamine, triethylenetetramine, tetraethylenepentamine, ethanolamine and hexamethylenediamine.

The designated primary amines are reacted either directly with the nitro-containing reaction products or with the compounds derivable therefrom, for example by reaction with bases, containing reactive carbonyl groups, as a rule at from 5 to 150° C., in particular 20 to 100° C., usually in a conventional inert organic or inorganic solvent and normally under atmospheric pressure.

The nitro-containing reaction products are hydrogenated, directly or as subsequent products, preferably by catalytic hydrogenation with hydrogen in the presence of hydrogenation catalysts, by transfer hydrogenation with organic or inorganic compounds with a reducing action, by reduction with base metals or by reduction with salt-like complex hydrides or salt-like low-valency sulfur compounds.

The hydrogenation can be carried out under atmospheric or super-atmospheric pressure, either continuously or batchwise, in the types of reactor customary for this purpose, such as stirred vessels, stirred vessel cascades, tubular reactors, bubble columns and combinations of these reactor types.

The hydrogenation is generally carried out in an inert solvent or diluent or mixture thereof. Examples suitable for this purpose are hydrocarbons such as n-hexane, isooctane, n-alkane mixture (eg. $C_9$–$C_{13}$), cyclohexane, toluene or tetralin, ethers such as diethyl ether, tert-butyl methyl ether or tetrahydrofuran, alcohols such as methanol, isopropanol or 2-ethylhexanol, esters such as ethyl or n-butyl acetate or amides such as dimethylformamide or N-methylpyrrolidone. If the reaction products are to be used as fuel additives, it is expedient to use the same solvent in which they will later be mixed with the fuel. The amounts of solvent are in general from 50 to 90% of the weight of the complete mixture. However, it is also possible to do without solvent.

The temperature of the hydrogenation can normally be varied in the range from 20° C. to 250° C. It depends on the reduction system used. A preferred temperature range for catalytic hydrogenation is from 150° C. to 220° C.

The hydrogen pressure in the catalytic hydrogenation can, as a rule, be adjusted from 1 bar to 300 bar, preferably from 100 bar to 200 bar.

The hydrogenation catalysts used in catalytic hydrogenation with hydrogen are, for example, noble metal catalysts such as platinum, palladium, ruthenium, rhodium, osmium or iridium, Raney catalysts such as nickel, cobalt, iron or copper, mixed catalysts containing, for example, nickel, zirconium, copper and molybdenum or copper, chromium, zinc and barium, or oxide and sulfide catalysts. The catalysts can be employed in pure form in homogeneous solution or heterogeneously in suspension or as supported catalysts. Examples of supports used are carbon, alumina, zirconium oxide, silicon dioxide or magnesium oxide.

The amount of the hydrogenation catalyst in batchwise catalytic hydrogenations is usually from 0.01 to 50%, preferably from 1 to 25%, of the weight of the nitro-containing reaction products.

Examples of organic or inorganic compounds with a reducing action for transfer hydrogenation are formic acid or hydrazine.

Reducing base metals suitable for the hydrogenation are, for example, iron, zinc or tin.

It is possible to use on reduction with salt-like complex hydrides in particular lithium aluminum hydride, diisobutylaluminum hydride, sodium borohydride or tributyltin hydride. An example of a salt-like low-valency sulfur compound suitable for the reduction in this case is an alkali metal dithionite.

The hydrogenation can be carried out either in the absence or in the presence of ammonia or primary, secondary or tertiary amines, diamines, polyamines, alkanolamines, ether amines, polyether amines or polyether alkanolamines (R$^4$NH$_2$, R$^4$R$^5$NH or (R$^4$)$_3$N). The one to three organic radicals in these amines are moreover in each case independently of one another the radicals R$^4$ and R$^5$ which are defined hereinafter. Addition of a primary or secondary amine of this type results, in particular, in incorporation of the added amine into the product. It is moreover possible for the resulting organic nitrogen compounds derived from the primary or secondary amines employed also to have several nitrogen-functional groups and alcoholic hydroxyl groups in the molecule.

The amount of added ammonia or amines can be up to 200%, preferably from 10 to 100%, of the weight of the nitro-containing reaction products. Besides ammonia, suitable for this purpose are the following amines, for example: methylamine, tert-butylamine, 2-ethylhexylamine, 1,2-ethylenediamine, hexamethylenediamine, 3-(N,N-dimethylamino)propylamine, benzylamine, aniline, p-methoxyaniline, m-phenylenediamine, dipropylenetriamine, 1,4-diaminocyclohexane, 4,4,-diaminodicyclohexylmethane, dimethylamine, diethanolamine, di(tridecyl) amine, pyrrolidine, morpholine, piperazine, triethylamine, N,N-dimethylaniline or pyridine.

The hydrogenation is advantageously carried out under neutral or basic reaction conditions.

Catalytic hydrogenations with hydrogen in the presence of hydrogenation catalysts are particularly advantageous for the process according to the invention because, when other reduction methods are used, sometimes residues of metals, metal salts, sulfur compounds or similar impurities remain in the reduction product and may adversely affect, on use as fuel and lubricant additive, the action of the exhaust gas catalyst of vehicles powered by otto engines.

Catalytic hydrogenations with hydrogen in the presence of hydrogenation catalysts are particularly advantageous for the process according to the invention because, when other reduction methods are used, sometimes residues of metals, metal salts, sulfur compounds or similar impurities remain in the reduction product and may adversely affect, on use as fuel and lubricant additive, the action of the exhaust gas catalyst of vehicles powered by otto engines.

The hydrogenation can be carried out either continuously or batchwise in the apparatus customary for this purpose.

$C_2$–$C_6$-Olefins which can be used for the olefin polymers employed as starting material are ethylene, propene, 1-butene, 2-butene, isobutene, 1,3-butadiene, 1-pentene, 2-pentene, 2-methyl-1-butene, 2-methyl-2-butene, 1,3-pentadiene, 1-hexene, 2-hexene, 3-hexene, 2-methyl-1-pentene, 2-methyl-2-pentene, 2-methyl-3-pentene, 2-methyl-4-pentene, 3-methyl-1-pentene, 3-methyl-2-pentene, 2-ethyl-1-butene, 3,3-dimethyl-1-butene, 1,3-hexadiene, 2,4-hexadiene, 1,5-hexadiene or 1,3,5-hexatriene. It is also possible to employ mixtures of said olefins. Of these, -propene, 1-butene, 2-butene, isobutene, 1,3-butadiene or mixtures thereof are preferred. A typical example of an olefin polymer of this type is polypropylene.

Nitro-containing reaction products which can be employed and are suitable for the process according to the invention are, in particular, those of polymers of isobutene with an average degree of polymerization P=5–100, where up to 50% by weight, preferably up to 30% by weight, of the isobutene can be replaced by other $C_2$–$C_6$-olefins, in particular by propene, 1-butene, 2-butene or 1,3-butadiene or a mixture thereof, as comonomers, with nitrogen oxides or mixtures of nitrogen oxides and oxygen.

Said $C_2$–$C_6$-olefins are, as a rule, polymerized by conventional methods. The polymers have, owing to chain-termination reactions, terminal ($\alpha$), $\beta$ and internal double bonds, with the $\beta$ and, in particular, the terminal double bonds being the preferred centers for the reaction with the nitrogen oxides.

The average degree of polymerization P for the above-mentioned embodiments is from 5 to 100, preferably 8 to 80, in particular 10 to 60, especially 15 to 40. As always with such polymerizations, the resulting polymers have a particular range of degrees of polymerization. However, the variation has no discernible effect on the properties of the reaction products with nitrogen oxides or nitrogen oxide/oxygen mixtures, so that only the average degree of polymerization P matters, and this can be continuously determined, for example by viscosity measurements, and controlled during the polymerization.

Correlating with the average degree of polymerization P, the described polyolefins have carbon numbers of from 10 to about 600, preferably 24 to about 320, in particular 40 to about 240, and average molecular weights (number average) of from 140 to 8400, preferably 330 to 4500, in particular 560 to 3400.

Generally suitable as nitrogen oxides for reaction with the described products are, in particular, nitrogen monoxide (NO), nitrogen dioxide ($NO_2$), dinitrogen trioxide ($N_2O_3$), dinitrogen tetroxide ($N_2O_4$), mixtures of these nitrogen oxides with one another and mixtures of these nitrogen oxides with oxygen, in particular No with oxygen and $NO_2$ with oxygen. When oxygen is also used, this accounts for 1 to 70% by volume, in particular 5 to 50% by volume, of the mixture with the nitrogen oxides. The nitrogen oxide/oxygen mixture may also contain inert gases, eg. nitrogen; this occurs, for example, when nitrogen oxide/air mixtures are used.

The reaction to give the described products can be carried out under atmospheric or superatmospheric pressure, batchwise or continuously.

In order to obtain a quantitative conversion, the nitrogen oxides are added in the polyolefin to nitrogen oxide molar ratio of from 1:2 to 1:4, preferably 1:2.2 to 1:3.3. A larger excess has no adverse effects.

The temperature is not critical. It may vary in the range from –30° to 150° C., preferably from –10° to 100° C., in particular from 25° C. to 80° C.

The reaction is advantageously carried out in an inert organic solvent. Examples suitable for this purpose are aliphatic hydrocarbons such as isooctane or an n-alkane mixture (eg. $C_{10}$–$C_{13}$), chlorinated hydrocarbons such as methylene chloride, tetrachloromethane or chlorobenzene, ethers such as diethyl ether, tetrahydrofuran, dioxane or tert-butyl methyl ether, esters such as ethyl acetate or methyl benzoate, amides such as dimethylformamide or N-methylpyrrolidone, and acids such as acetic acid. In general, the amounts of solvent are from 50 to 90% of the weight of the complete mixture. However, it is also possible to do without solvent.

Addition of a small amount of water (about 0.2 to 1% of the weight of polyolefin) in order to hydrolyze any nitrite ester formed has no adverse effects.

A reaction mixture is usually worked up by briefly heating to 40 to 50° C. under reduced pressure or stirring with water and subsequently carrying out a phase separation. The aim of both measures is to remove residues of nitrogen oxides from the reaction mixture.

As a rule, the described nitro-containing reaction products result, especially when $NO_2$ has been employed or also used as nitrogen oxide, in the form of a mixture of various nitro-containing alkanes.

Further nitro-containing reaction products which are suitable and can be employed for the process according to the invention are, in particular, those of polymers of $C_2$–$C_6$-olefins with an average degree of polymerization P=5–100 and nitrogen oxides or mixtures of nitrogen oxides and oxygen, which are in the form of a mixture of various nitro-containing alkanes and contain as main components the compounds of the general formula I and II

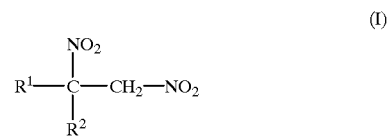
(I)

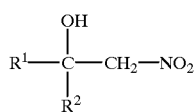

(II)

$R^1$ is a long-chain linear or branched alkyl radical with 8–600, preferably 20–450, in particular 40–300, carbon atoms and
$R^2$ is hydrogen or $C_1$–$C_3$-alkyl.

The compounds I and II are derived from olefin polymers with terminal double bonds.

Further nitro-containing reaction products which are suitable and can be employed for the process according to the invention are, in particular, those of polymers of $C_2$–$C_6$-olefins with an average degree of polymerization P5–100 and a high content of β double bonds and a low content of terminal double bonds with nitrogen oxides or mixtures of nitrogen oxides and oxygen, which are in the form of a mixture of various nitro-containing alkanes and contain as main components the compounds of the general formula III and IV

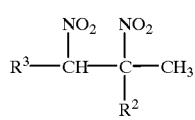

(III)

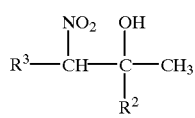

(IV)

where
$R^3$ is a long-chain linear or branched alkyl radical with 8–600, preferably 20–450, in particular 40–300, carbon atoms and
$R^2$ is hydrogen or $C_1$–$C_3$-alkyl.

In this case, the radical $R^3$ is a radical $R^1$ which has been shortened by a carbon atom or a $CH_2$ group.

Further nitro-containing reaction products which are suitable and can be employed for the process according to the invention are, in particular, those of polyisobutenes with an average degree of polymerization P=10–100 with a content E=60–90% of double bonds able to react with maleic anhydride, where E=100% would correspond to the calculated theoretical value for the case where each molecule of polyisobutene had such a reactive double bond, with nitrogen oxides or mixtures of nitrogen oxides and oxygen. The average degree of polymerization P for the described highly reactive polyisobutenes is from 10 to 100, preferably from 15 to 40. Correlating with the average degree of polymerization P, the described highly reactive polyisobutenes have carbon numbers of from 36 to 400, preferably 54 to 160 and average molecular weights (number average) of from 500 to 5600, preferably 750 to 2250.

The term polyisobutenes as starting materials for the present invention means not only the homopolymers of isobutene but also its copolymers with an isobutene content of at least 80%. Suitable comonomers are, primarily, the other $C_4$ olefinic hydrocarbons so that it is possible to start directly from the $C_4$ cuts, which is of particular industrial significance. Although these contain only 35–45% isobutene, besides 12–14% butanes, 40–55% butenes and up to 1% butadiene, the substantially selective polymerizability of isobutene means that the other monomers are incorporated only to the extent of about 2–20% into the polymer under the polymerization conditions. The monomers which have not reacted can be used for other purposes. Further suitable comonomers are $C_3$ monomers such as propene, and ethylene or mixtures thereof or with $C_4$ monomers.

This process results in isobutenes with a content E of double bonds able to react with maleic anhydride of from 60 to 90 percent, in many cases from 75 to 90 percent. The calculated theoretical value E=100% would accordingly mean that each polyisobutene molecule contained such a reactive double bond. E can be determined in a simple manner and most reliably directly from the acid number of the polyisobutene/maleic anhydride adduct.

With regard to the nitrogen oxides to be employed and the reaction conditions, what has been said above for the reaction of $C_2$–$C_6$-olefin polymers applies in the same way to the highly reactive polyisobutenes described.

Further nitro-containing reaction products which are suitable and can be employed for the process according to the invention are, in particular, those of polyisobutenes with an average degree of polymerization P=10–100 with a content E=60–90% of double bonds able to react with maleic anhydride, where E=100% would correspond to the calculated theoretical value for the case where each molecule of the polyisobutene had such a reactive double bond, with nitrogen oxides or mixtures of nitrogen oxides and oxygen, which are in the form of a mixture of various nitro-containing alkanes and contain as main components the compounds of the general formula V to VIII

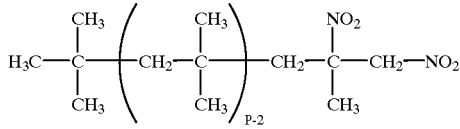

(V)

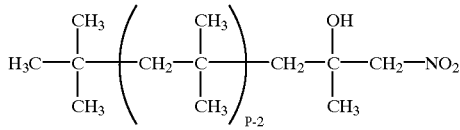

(VI)

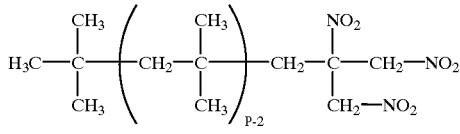

(VII)

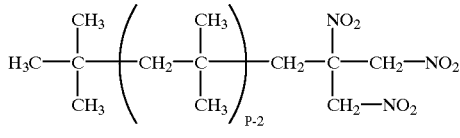

(VIII)

Surprisingly, in the process according to the invention, the products derived directly by reduction of the nitro groups, such as the corresponding diamine from the dinitro compound I, are formed in only minor amounts, if at all. Depending on the reaction conditions, the main products obtained are aminoalkanes, alkyloximes and/or alkylnitrones of the structures IX to XI or XII to XIV:

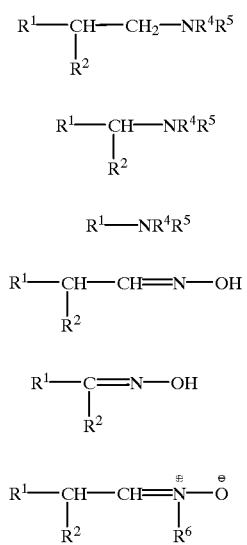

(IX)
$$R^1-CH-CH_2-NR^4R^5$$
$$|$$
$$R^2$$

(X)
$$R^1-CH-NR^4R^5$$
$$|$$
$$R^2$$

(XI)
$$R^1-NR^4R^5$$

(XII)
$$R^1-CH-CH=N-OH$$
$$|$$
$$R^2$$

(XIII)
$$R^1-C=N-OH$$
$$|$$
$$R^2$$

(XIV)
$$R^1-CH-CH=\overset{\oplus}{N}-\overset{\ominus}{O}$$
$$|\quad\quad |$$
$$R^2\quad R^6$$

where
$R^1$ is a long-chain linear or branched alkyl radical with 8–600, preferably 20–450, in particular 40–300, carbon atoms,
$R^2$ is hydrogen or $C_1$–$C_3$-alkyl,
$R^4$ and $R^5$ are, independently of one another, hydrogen, $C_1$–$C_{30}$-alkyl or $C_3$–$C_{30}$-alkenyl, which can be interrupted by non-adjacent oxygen atoms or by $NR^2$ groups or can carry hydroxyl groups, $C_5$–$C_8$-cycloalkyl, $C_7$–$C_{18}$-aralkyl, unsubstituted or substituted $C_6$–$C_{14}$-aryl, amine, diamine or polyamine radicals of the formula $-(-A-NR^7-)_m-R^8$, alkanolamine radicals of the formula $-A-OH$, ether amine, oligo- and polyether amine radicals of the formula $-(A-O)_m-R^7$ or oligo- and polyether alkanolamine radicals of the formula $-(A-O)_m-A-OH$, where A is $C_2$–$C_{10}$-alkylene, $C_5$–$C_{18}$-cycloalkylene or phenylene, $R^7$ and $R^8$ are hydrogen or $C_1$–$C_8$-alkyl and m is a number from 1 to 8, where the two radicals $R^4$ and $R^5$ can also form a five- or six-membered ring, and
$R^6$ is $C_1$–$C_3$-alkyl.

The meaning of the organic radicals $R^4$ and $R^5$ on the amine nitrogen corresponds to those of the organic radicals in the primary amine used previously for the imine formation.

The meaning of $R^6$ as a rule corresponds to that of $R^3$.

If neither of the radicals $R^4$ and $R^5$ is hydrogen, the corresponding organic radicals $R^4$ and $R^5$ for the purpose of the present invention derive from, as described hereinbefore, the primary or secondary amines added in the hydrogenation. What has been stated above applies to the meanings of $R^4$ and $R^5$ in these amines.

Accordingly, the present invention also relates to those mixtures of aminoalkanes and, where appropriate, alkyloximes and alkylnitrones with the same long-chain radicals which contain the compounds of the general formula IX to XII as main components.

The present invention furthermore also relates to those mixtures of alkyloximes and alkylnitrones and, where appropriate, aminoalkanes with the same long-chain radicals which contain the compounds of the general formula XII to XIV as main components.

The three stated main components of the two mixtures according to the invention are normally in the ratio by weight of (1–98):(1–98):(1–98), in particular (5–90):(5–90): (5–90), in each case. This ratio can be adjusted by the choice of the reaction parameters.

The structures IX to XIV, and the carbonyl and imine precursors of these final products, can be isolated by conventional methods from the resulting mixtures and thus obtained in pure form. Subsequent enrichment of the relevant structures in the resulting mixtures is also possible. These isolated individual structures show at least equally good use properties. It is also possible in many cases to obtain said individual structures in virtually pure form or at least in greatly enriched form directly from the corresponding reaction by suitable choice of the reaction parameters.

The present invention therefore also relates to each of the following individual compounds:

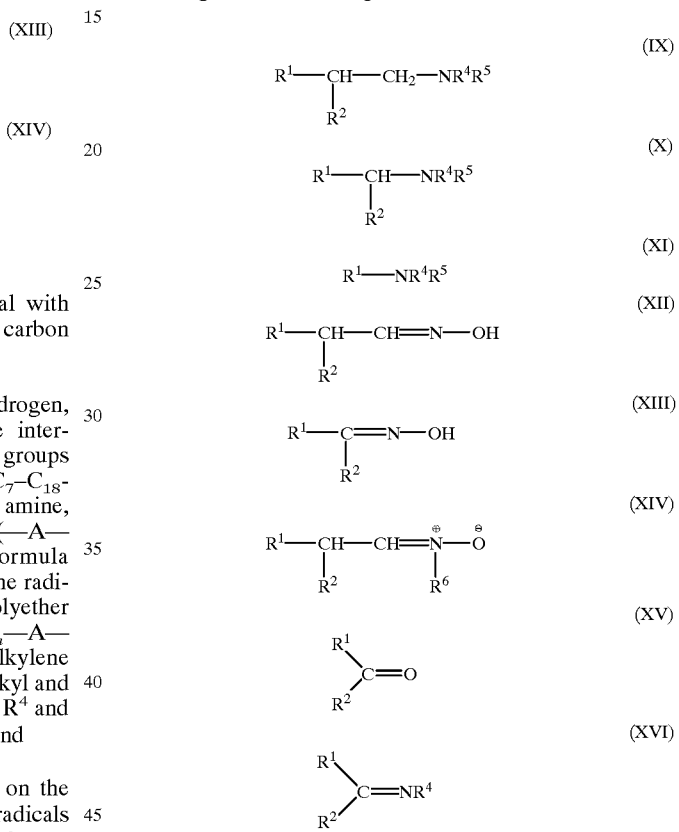

The radicals $R^1$, $R^2$, $R^4$, $R^5$ and $R^6$ have the abovementioned meanings.

In a preferred embodiment, the radical $R^1$ in the mixtures and compounds according to the invention has the meaning

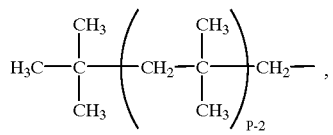

where the degree of polymerization P=10–100, and the radicals $R^2$ and $R^6$ are methyl.

Furthermore, the mixtures and compounds according to the invention which are preferred are those where the radicals $R^4$ and $R^5$ are both hydrogen.

Besides the main products IX to XIV, the mixtures according to the invention may also contain the following compounds as by-products:

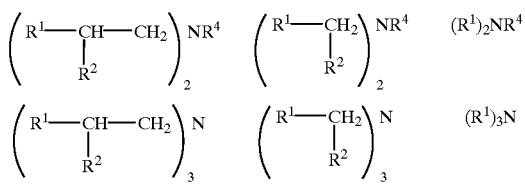

Further byproducts which are sometimes found are alcohols of the formula $R^1$—$CHR^2$—$CH_2OH$, $R^1$—$CHR^2$—$OH$ and/or $R^1$—$OH$.

The aminoalkanes, alkyloximes, alkylnitrones and mixtures thereof prepared by the process according to the invention, but especially the mixtures according to the invention with the structures IX to XI and XII to XIV as main components, and the compounds IX to XVI according to the invention themselves, are outstandingly suitable as additives for fuels and lubricants. The present invention therefore likewise relates to fuels for otto engines and lubricants with such additives.

If the described products are employed in fuels, they are preferably added in an amount of from 10 to 5000 ppm, in particular 50 to 1000 ppm. A higher additive content is usually necessary in lubricants, and the amounts in this case can be from 0.1 to 6% by weight, in particular 0.5 to 5% by weight.

If the intention primarily is to utilize the dispersant properties of the products, they can also be combined with conventional detergents as additional additives.

It is possible in principle to employ as detergent component in the mixture with the substances according to the invention as dispersants all of the known products suitable for this purpose, as described, for example, by J. Falbe, U. Hasserodt, Katalysatoren, Tenside und Mineralöladditive, G. Thieme Verlag Stuttgart, 1978, pages 223 et seq., or by K. Owen, Gasoline and Diesel Fuel Additives, John Wiley & Sons, 1989, pages 23 et seq.

N-containing detergents are preferably used, eg. compounds which contain an amine or amide group. Particularly suitable are polyisobutylamines disclosed in EP-A 244 616, ethylenediaminetetra-acetamides and/or -imides disclosed in EP-A 356 725, reference being made to the definitions in these citations. The products described therein likewise have the advantage, like the described products, of being free of chlorine and chloride owing to the preparation.

If the intention primarily is to utilize the detergent action of the reaction products according to the invention, these substances can also be combined with carrier oils. Such carrier oils are known, and particularly suitable carrier oils are based on polyglycols, eg. corresponding ethers and/or esters as described in U.S. Pat. No. 5,004,478 or DE-A 38 38 918. It is also possible to employ polyoxyalkylenemonools with hydrocarbon end groups (U.S. Pat. No. 4,877,416) or carrier oils as disclosed in DE-A 41 42 241.

Suitable fuels for otto engines are leaded and, in particular, unleaded normal and supergasoline. The gasolines may also contain components other than hydrocarbons, eg. alcohols such as methanol, ethanol or tert-butanol, and ethers, eg. methyl tert-butyl ether. Besides the reaction products according to the invention, the fuels usually also contain further additives such as corrosion inhibitors, stabilizers, antioxidants and/or other detergents.

Corrosion inhibitors are usually ammonium salts of organic carboxylic acids which, owing to an appropriate structure of the starting compounds, are prone to film formation. Corrosion inhibitors also frequently contain amines to reduce the pH. Heterocyclic aromatic compounds are usually employed as nonferrous metal corrosion inhibitors.

The products were tested for suitability as fuel additives by engine tests; in bench tests as specified in CEC-F-05-T-92, the keep-clean action with inlet valves (Mercedes-Benz M 102 E engine) was tested.

PREPARATION EXAMPLES

Example 1

10 g of the reaction product from highly reactive polyisobutene (Glissopal® ES 3250) and nitrogen dioxide (according to Example 4 of (1)), 80 ml of tetrahydrofuran, 15 ml of methanol and 5 g of Raney nickel were introduced into a 300 ml autoclave. Oxygen was removed from the gas space by injecting 20 bar of nitrogen and subsequent decompression on two occasions. After adding 15 g of ammonia, 100 bar of hydrogen were injected, and the mixture was heated to 200° C. Further hydrogen was injected to 200 bar. The contents of the autoclave were stirred at 200° C. and 200 bar for 10 hours. The cooled discharge was filtered, and the filtrate was evaporated under reduced pressure. 7 g of residue with an amine number of 53 mg KOH/g were obtained.

The product mainly consisted of $X^1NH_2$ and $X^2NH_2$ in addition to $X^3NH_2$ and traces of secondary amines ($X^1NH_2$: 30% by weight, $X^2NH_2$: 60% by weight, $X^3NH_2$: 10% by weight).

Example 2

180 g of reaction product from highly reactive polyisobutene (Glissopal ES 3250) and nitrogen dioxide (according to Example 4 of (1)), 900 g of Mihagol® M ($C_{10}$–$C_{14}$ n-alkane mixture) and 45 g of Raney nickel were introduced into a 3.5 l autoclave. Oxygen was removed from the gas space by injecting 20 bar of nitrogen and subsequent decompression on two occasions. Then 70 bar of hydrogen were injected, and the mixture was heated to 200° C. Further hydrogen was injected to 200 bar, and the autoclave was stirred at 200° C. and 200 bar for 10 hours. After cooling, the reaction mixture was filtered and distilled under reduced pressure to remove solvent and the ammonia formed in the reaction. 168 g of an oil with an amine number of 36 mg KOH/g and an OH number of 8 mg KOH/g remained.

The product mainly consisted of $X^1NH_2$ and $X^2NH_2$ in addition to $X^3NH_2$ and $X^1OH$.

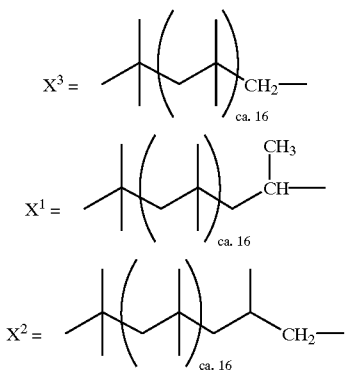

Example 3 a) 20 g of reaction product from highly reactive polyisobutene (Glissopal ES 3250) and nitrogen dioxide (according to Example 4 of (1)), 100 ml of tetrahydrofuran and 6.5 g of 3-dimethylaminopropylamine were introduced into a 200 ml stirred vessel and stirred at 40° C. for 3 hours. Then the volatile constituents were removed by distillation under reduced pressure. The 21 g of oily residue contained, besides residual 3-dimethylaminopropylamine, as main product the 3-dimethylaminopropylimine of a keto-polyisobutene:

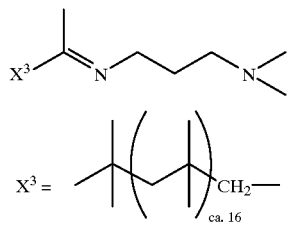

b) 20 g of the oily residue were introduced with 100 ml of tetrahydrofuran and 5 g of Raney nickel into a 300 ml autoclave. Oxygen was removed from the gas space by injecting 20 bar of nitrogen and subsequent decompression on two occasions. 50 bar of hydrogen were injected and the mixture was heated to 150° C., the pressure was increased to 100 bar with hydrogen and the mixture was stirred under these conditions for 10 hours. After cooling, the nickel was filtered off and the volatiles were removed by distillation under reduced pressure, finally at 120° C. under 1 mbar. 16.9 g of residue with an amine number of 77 mg KOH/g were obtained.

The product comprised about 75% by weight of

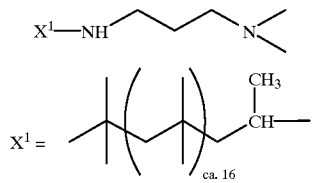

Example 4

100 ml of dry tetrahydrofuran and 4.6 g of lithium aluminum hydride were introduced into a 1 l stirred apparatus flushed with nitrogen. Then a solution consisting of 30 g of reaction product from highly reactive polyisobutene (Glissopal ES 3250) and nitrogen dioxide (according to Example 4 of (1)) and 100 ml of dry tetrahydrofuran was added dropwise at such a rate that the temperature in the flask was kept at 40–50° C. After the dropwise addition, the mixture was stirred at room temperature for 2 hours and then the excess lithium aluminum hydride was cautiously hydrolyzed with water. The reaction mixture was filtered with suction through kieselguhr, and the filtrate was concentrated under reduced pressure. 26.5 g of residue with an amine number of 33 mg KOH/g were obtained.

The product consists of about 75% by weight $X^2NH_2$ and about 25% by weight $X^1OH$:

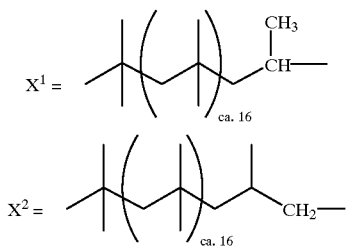

Example 5

50 g of reaction product from highly reactive polyisobutene (Glissopal ES 3250) and nitrogen dioxide (according to Example 4 of (1)), 200 ml of tetrahydrofuran and 10 g of catalyst HO-50 (50% by weight water; 2.5% by weight palladium; 47.5% by weight carbon) were introduced into a 0.5 l autoclave. Oxygen was removed from the gas space by injecting 5 bar of hydrogen and subsequent decompression on two occasions. The mixture was heated to 50° C. and further hydrogen was injected to 7 bar. The contents of the autoclave were stirred at 50° C. and 7 bar for 7 hours. The hydrogen uptake during this was 22.3 bar (equivalent to 5.6 l). The cooled reaction mixture was filtered and the filtrate was evaporated.

The residue consisted mainly of the substances

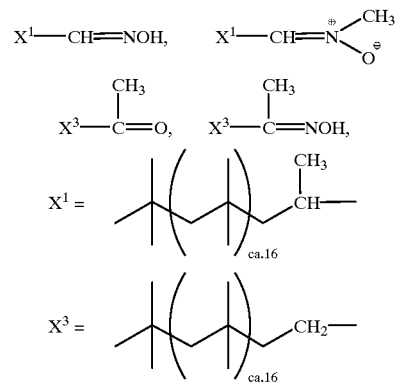

Example 6

20 g of reaction product from highly reactive polyisobutene (Glissopal ES 3250) and nitrogen dioxide (according to Example 4 of (1)), 100 ml of tetrahydrofuran and 5 g of Raney nickel were introduced into a 300 ml autoclave. Oxygen was removed from the gas space by injecting 20 bar of nitrogen and subsequent decompression on two occasions. After adding 22 g of methylamine, 50 bar of hydrogen were injected and the mixture was heated to 200° C. Further hydrogen was injected to 200 bar and the autoclave was stirred at 200° C. and 200 bar for 10 hours. The cooled reaction mixture was filtered and the filtrate was evaporated under reduced pressure. 17.4 g of residue with an amine number of 46 mg KOH/g were obtained.

The product consisted mainly of: $X^3NHCH_3$, $X^1NHCH_3$, $X^2NHCH_3$ and $X^1NH_2$

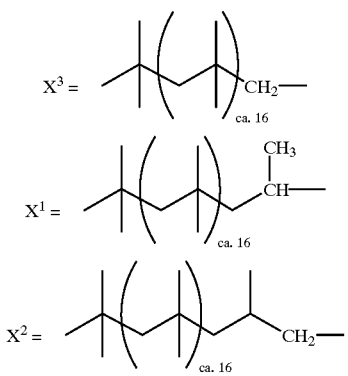

Example 7

20 g of reaction product from highly reactive polyisobutene (Glissopal ES 3250) and nitrogen dioxide (according to Example 4 of (1)), 100 ml of tetrahydrofuran and 5 g of Raney nickel were introduced into a 300 ml autoclave. Oxygen was removed from the gas space by injecting 20 bar of nitrogen and subsequent decompression on two occasions. After adding 32 g of dimethylamine, 50 bar of hydrogen were injected and the mixture was heated to 200° C. Further hydrogen was injected to 200 bar and the autoclave was stirred at 200° C. and 200 bar for 10 hours. The cooled reaction mixture was filtered and the filtrate was evaporated under reduced pressure. 16 g of residue with an amine number of 40 mg KOH/g were obtained.

The product mainly consists of:

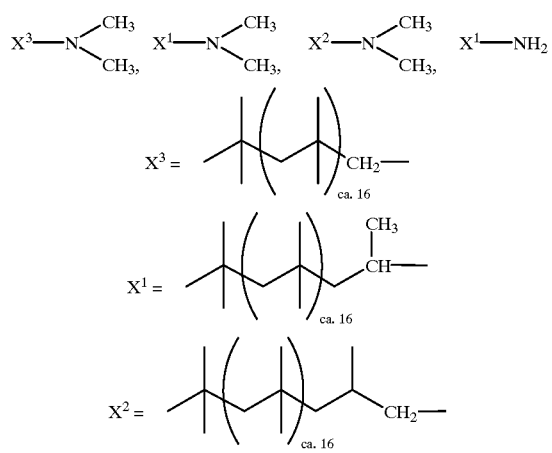

Example 8

100 ml of dry tetrahydrofuran and 4 g of lithium aluminum hydride were introduced into a 0.5 l stirred apparatus which had been flushed with nitrogen. Then a solution consisting of 100 ml of tetrahydrofuran and 50 g of nitropolyisobutene (according to Example 8 of (1)), which is obtained when the reaction product from highly reactive polyisobutene (Glissopal ES 3250) and nitrogen dioxide (according to Example 4 of (1)) is stirred with an aqueous sodium carbonate solution and consists of (XVI) in addition to (XV), was added dropwise at such a rate that the temperature in the flask was kept at 45–50° C. After the dropwise addition, the mixture was stirred at room temperature for 3 hours and then cautiously hydrolyzed with 5 g of water. The reaction mixture was filtered with suction through kieselguhr and the filtrate was concentrated under reduced pressure.

41 g of oil with an amine number of 33 mg KOH/g and the same composition as the product from Example 4, ie. about 75% by weight $X^2NH_2$ and about 25% by weight $X^1OH$, were obtained.

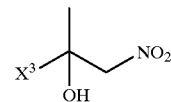

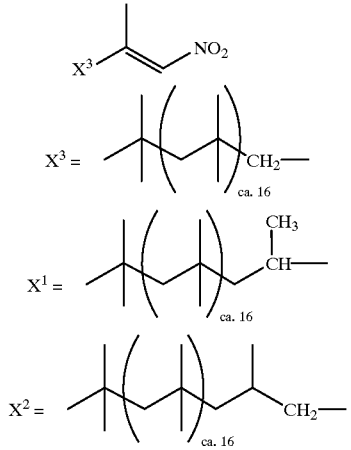

Example 9

10 g of keto-polyisobutene of the formula $X^3$—CO—$CH_3$, which is produced by stirring the reaction product from highly reactive polyisobutene (Glissopal ES 3250) and nitrogen dioxide (according to Example 4 of (1)) with an aqueous ammonia solution at 25° C., 80 ml of tetrahydrofuran, 15 ml of methanol and 5 g of Raney nickel were introduced into a 300 ml autoclave. Oxygen was removed from the gas space by injecting 20 bar of nitrogen and subsequent decompression on two occasions. After adding 12.5 g of ammonia, 70 bar of hydrogen were injected and the mixture was heated to 200° C. Further hydrogen was injected to 200 bar, and the autoclave was stirred at 200° C. and 200 bar for 10 hours. The cooled reaction mixture was filtered and the filtrate was concentrated under reduced pressure. 8.8 g of residue with an amine number of 43.5 mg KOH/g were obtained.

The product consisted mostly of $X^1NH_2$.

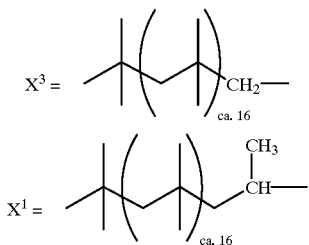

Example 10

20 g of keto-polyisobutene of the formula $X^3$—Co—$CH_3$, which is produced by stirring the reaction product from highly reactive polyisobutene (Glissopal ES 3250) and nitrogen dioxide (according to Example 4 of (1)) with an aqueous ammonia solution at 25° C., 100 ml of tetrahydrofuran, 6.2 g of 3-dimethylaminopropylamine and 5 g of Raney nickel were introduced into a 300 ml autoclave. Oxygen was removed from the gas space by injecting 20 bar of nitrogen and subsequent decompression on two occasions. Then 50 bar of hydrogen were injected and the mixture was heated to 150° C. Further hydrogen was injected to 100 bar and the mixture was stirred at 150° C. and 100 bar for 10 hours. The cooled autoclave contents were filtered and the filtrate was evaporated under reduced pressure, finally at 80° C. under 1 mbar. 20 g of residue with an amine number of 108 mg KOH/g, which was divided into 12 mg KOH/g for primary, 44 mg KOH/g for secondary and 51 mg KOH/g for tertiary amines, were obtained.

The product consisted of:

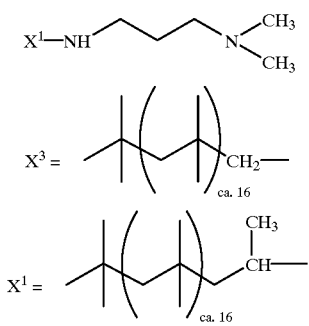

Examples 11a to e 20 g of reaction product from highly reactive polyisobutene (Glissopal ES 3250) and nitrogen dioxide (according to Example 4 of (1)), 20 g of Mihagol M ($C_{10}$–$C_{14}$ n-alkane mixture), 100 g of tetrahydrofuran and 2.5 g or 5 g of catalyst shown in the following table were introduced into a 300 ml autoclave. Oxygen as removed from the gas space by injecting 20 bar of nitrogen and subsequent decompression on two occasions. After adding 15 g of ammonia, 100 bar of hydrogen were injected and the mixture was heated to 200° C. Further hydrogen was injected to 200 bar. The autoclave contents were stirred at 200° C. and 200 bar for 10 hours. The cooled discharge was filtered and the filtrate was evaporated under reduced pressure. 17 g of residue with an amine number of 30–50 mg KOH/g were obtained (see table).

The product mainly consisted in all 5 examples of $X^1NH_2$ and $X^2NH_2$ in addition to $X^3NH_2$ and, where appropriate, secondary amines (maximum 5% by weight).

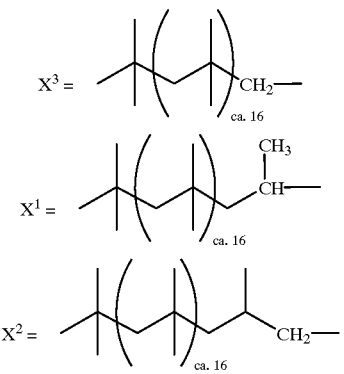

TABLE for Examples 11a to e

| Example | Catalyst | Amine number | Product composition [% by weight] | | |
|---|---|---|---|---|---|
| | | | $X^1NH_2$ | $X^2NH_2$ | $X^3NH_2$ |
| 11a | 5 g ruthenium on carbon 5 % by weight; moist (50 % by weight) | 52 | 75 | 10 | 10 |
| 11b | 2.5 g rhodium on carbon 5 % by weight; dry | 52 | 30 | 55 | 10 |
| 11c | 5 g platinum on carbon 5 %; moist (50 % by weight) | 33 | 30 | 60 | 5 |
| 11d | 5 g H 0–50: palladium on carbon 5 % by weight; moist (50 % by weight) | 50 | 50 | 40 | 10 |
| 11e | 5 g H 1–88: commercial mixed catalyst (Ni, Zr, Cu, Mo) | 48 | 40 | 55 | 5 |

Example 12

The reaction mixture from Example 5 was introduced with 100 ml of tetrahydrofuran and 10 g of Raney nickel into a 300 ml autoclave. Oxygen was removed from the gas space by injecting 20 bar of nitrogen and subsequent decompression on two occasions. After addition of 15 g of ammonia, the mixture was heated to 100° C. and hydrogen was injected to 100 bar. The autoclave was stirred at 100° C. and 100 bar for 10 hours. After cooling, the reaction mixture was filtered and the filtrate was evaporated. 24 g of residue with an amine number of 32 mg KOH/g remained.

Example 13

10 g of reaction product from polyisobutene with a high content of β double bonds (Indopol® H100) and nitrogen dioxide (according to Example 2 of (2)), 80 ml of tetrahydrofuran and 15 ml of methanol and 5 g of Raney nickel were introduced into a 300 ml autoclave. Oxygen was removed from the gas space by injecting 20 bar of nitrogen and subsequent decompression on two occasions. After adding 15 g of ammonia, 70 bar of hydrogen were injected and the mixture was heated to 200° C. Further hydrogen was injected to 200 bar and the autoclave was stirred at 200° C. and 200 bar for 10 hours. The cooled reaction mixture was filtered and the filtrate was evaporated under reduced pressure. 8.2 g of residue with an amine number of 56 mg KOH/g were obtained.

Example 14

150 g of reaction product from oligopropen (average molecular weight about 378, Br number 43, vinylidene-terminated) and nitrogen dioxide, 1000 ml of tetrahydrofuran and 38 g of Raney nickel were introduced into a 3.5 l autoclave. Oxygen was removed from the gas space by injecting 20 bar of nitrogen and subsequent decompression on two occasions. After adding 90 g of ammonia, 100 bar of hydrogen were injected, and the mixture was heated to 200° C. Further hydrogen was injected to 200 bar and the autoclave was stirred at 200° C. and 200 bar for 10 hours. The cooled reaction mixture was filtered and the filtrate was evaporated. 118 g of residue with an amine number of 127.4 mg KOH/g, nitrogen content 3.8% by weight, were obtained.

The product consisted mainly of $Y^1NH_2$ and $Y^2NH_2$.

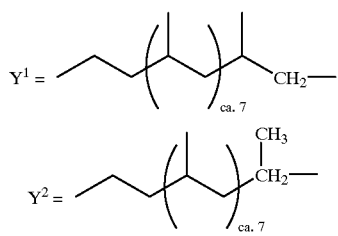

Example 15

100 ml of dry tetrahydrofuran and 8 g of lithium aluminum hydride were introduced into a 0.5 l stirred apparatus flushed with nitrogen. Then a solution consisting of 25 g of reaction product from oligopropene (average molecular weight about 378, bromine number 43, vinylidene-terminated) and nitrogen dioxide and 100 ml of tetrahydrofuran was added dropwise at such a rate that the temperature in the flask was kept at about 40° C. After the dropwise addition, the mixture was stirred at room temperature for 3 hours and then the excess lithium aluminum hydride was cautiously hydrolyzed with a little water. The reaction mixture was filtered with suction through kieselguhr and the filtrate was evaporated under reduced pressure. 18.2 g of residue with an amine number of 84.4 were obtained.

The product consisted mainly of $Y^1NH_2$ and $Y^2$—OH.

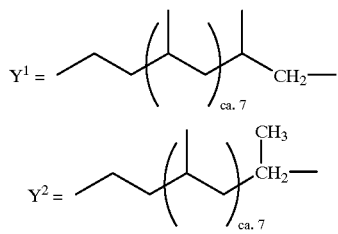

Example 16

20 g of reaction product from oligopropene (average molecular weight about 336, bromine number 47.5, about 90% vinyl-terminated) and nitrogen dioxide (similar to Example 1 of (2)), 100 ml of tetrahydrofuran and 5 g of Raney nickel were introduced into a 300 ml autoclave. Oxygen was removed from the gas space by injecting 20 bar of nitrogen and subsequent decompression on two occasions. After adding 20 g of ammonia, 50 bar of hydrogen were injected and the mixture was heated to 200° C. Further hydrogen was injected to 200 bar and the autoclave was stirred at 200° C. and 200 bar for 10 hours. The cooled reaction mixture was filtered and evaporated under reduced pressure. 15.5 g of residue with an amine number of 153 mg KOH/g and a nitrogen content of 4.4% by weight were obtained.

The product consisted mainly of $Z^1NH_2$.

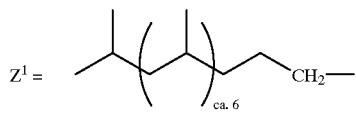

Example 17

100 ml of dry tetrahydrofuran and 8 g of lithium aluminum hydride were introduced into a 0.5 l stirred apparatus flushed with nitrogen. Then a solution consisting of 25 g of reaction product from an oligopropene (average molecular weight about 336, bromine number 47.5, about 90% vinyl-terminated) and nitrogen dioxide (similar to Example 1 of (2)) and 100 ml of tetrahydrofuran was added dropwise at such a rate that the temperature in the flask was kept at 40° C. After the dropwise addition, the mixture was stirred at room temperature for 3 hours and then cautiously hydrolyzed with a little water. The reaction mixture was filtered with suction through kieselguhr and the filtrate was evaporated under reduced pressure. 18 g of residue with an amine number of 84.3 were obtained.

The product consisted mainly of $Z^1NH_2$ and $Z^2NH_2$.

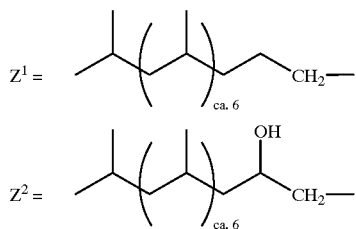

Example 17 merely serves for comparison purposes and illustrates one embodiment of (2).

Use Examples

Keep-clean test with inlet valves

The engine tests were carried out with a Mercedes-Benz M 102 E engine (in accordance with CEC-F-05-T-92):

Fuel employed: Euro-Super lead free

| Additive | Dosage | Inlet valve deposits [mg] | | | | |
|---|---|---|---|---|---|---|
| | [ppm] | Valve 1 | Valve 2 | Valve 3 | Valve 4 | Average |
| Product from Example 1 | 300 | 45 | 48 | 50 | 131 | 69 |
| for comparison: dinitroalkane of Ex. 4 of (1) | 400 | 187 | 31 | 166 | 145 | 132 |
| none (blank) | — | 309 | 420 | 312 | 303 | 336 |

The results clearly show the excellent valve-cleaning effect of the additives according to the invention, which is evident even at a relatively low dose rate.

We claim:

1. A mixture of aminoalkanes which contain as main components the compounds of formula IX to XI

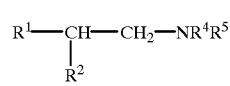 (IX)

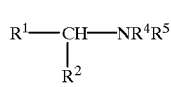 (X)

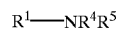 (XI)

where

R$^1$ is a long-chain linear or branched alkyl radical with 8–600 carbon atoms,

R$^2$ is hydrogen or C$_1$–C$_3$-alkyl, and

R$^4$ and R$^5$ are, independently of one another, hydrogen, C$_1$–C$_{30}$-alkyl or C$_3$–C$_{30}$-alkenyl, which can be interrupted by non-adjacent oxygen atoms or by NR$^2$ groups or can carry hydroxyl groups, C$_5$–C$_8$-cycloalkyl, C$_7$–C$_{18}$-aralkyl, unsubstituted or substituted C$_6$–C$_{14}$-aryl, amine, diamine or polyamine radicals of the formula —(—A—NR$^7$—)$_m$—R$^8$, alkanolamine radicals of the formula —A—OH, ether amine, oligo- and polyether amine radicals of the formula —(A—O)$_m$—R$^7$ or oligo- and polyether alkanolamine radicals of the formula —(A—O)$_m$—A—OH, where A is C$_2$–C$_{10}$-alkylene, C$_5$–C$_{18}$-cycloalkylene or phenylene, R$^7$ and R$^8$ are hydrogen or C$_1$–C$_8$-alkyl and m is a number from 1 to 8, where the two radicals R$^4$ and R$^5$ can also form a five- or six-membered ring.

2. A process for preparing an organic nitrogen compound having only one nitrogen-functional group and no alcoholic hydroxyl groups attached, which process comprises reacting a polymer of a C$_2$–C$_6$-olefin having an average degree of polymerization of from 5 to 100, with a nitrogen oxide or a mixture of a nitrogen oxide and oxygen to form a nitro-containing reaction product; hydrogenating the nitro-containing reaction product; and then recovering the organic nitrogen compound.

3. The process of claim 2 wherein the organic nitrogen compound prepared is selected from the group consisting of an aminoalkane.

4. The process of claim 2, wherein the hydrogenation is carried out as catalytic hydrogenation with hydrogen in the presence of hydrogenation catalysts, as transfer hydrogenation with organic or inorganic compounds with a reducing action, as reduction with base metals or as reduction with salt-like complex hydrides or salt-like low-valency sulfur compounds.

5. A process of claim 2, wherein the hydrogenation is carried out under neutral or basic reaction conditions.

6. The process of claim 2, wherein the hydrogenation is carried out at a temperature of from 20 to 250° C.

7. The process of claim 2, where the polymer of a C$_2$–C$_6$-olefin used is a polymer of isobutene, where up to 50% by weight of the isobutene can be replaced by another C$_2$–C$_6$-olefin as a comonomer.

8. The process of claim 2, wherein the nitro-containing reaction product is a mixture of various nitro-containing alkanes and contain as main components compounds of formula I and II

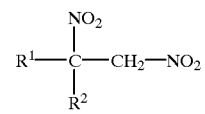 (I)

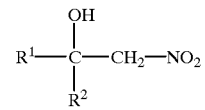 (II)

where

R$^1$ is a long-chain linear or branched alkyl radical with 8–600 carbon atoms; and R$^2$ is hydrogen or C$_1$–C$_3$-alkyl.

9. The process of claim 2, wherein the nitro-containing reaction product is a mixture of nitro-containing alkanes and contains as main components compounds of formula III and IV

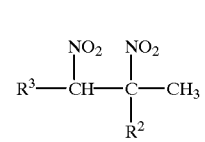 (III)

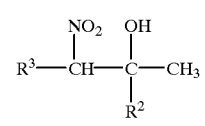 (IV)

where

R$^3$ is a long-chain linear or branched alkyl radical with 8–600 carbon atoms; and R$^2$ is hydrogen or C$_1$–C$_3$-alkyl.

10. The process of claim 2, wherein the polymer of a C$_2$–C$_6$-olefin is a polyisobutene having an average degree of polymerization of from 10 to 100 and with a content E=60–90% of double bonds able to react with maleic anhydride.

11. The process of claim 2, wherein the polyisobutene is in the form of a mixture of nitro-containing alkanes and contain as main components compounds of formula V to VIII

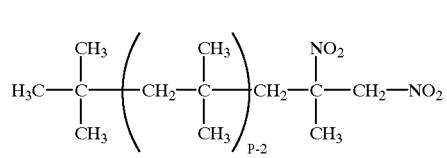 (V)

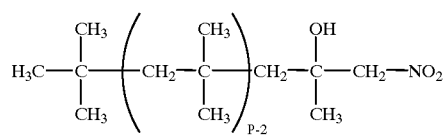 (VI)

-continued

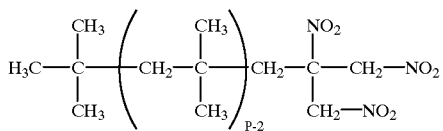
(VII)

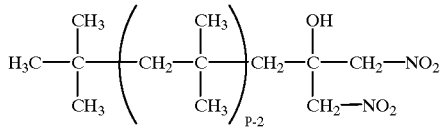
(VIII)

12. The process of claim 2 in which a polymer of a $C_3$–$C_6$-olefin is used.

13. The process of claim 12 in which the $C_3$–$C_6$-olefin is selected from the group consisting of propene, 1-butene, 2-butene and isobutene.

14. A process for preparing an organic nitrogen compound having at least two nitrogen-functional groups and at least one alcoholic hydroxyl group attached, which process comprises reacting a polymer of a $C_2$–$C_6$-olefin having an average degree of polymerization of from 5 to 100, with a nitrogen oxide or a mixture of a nitrogen oxide and oxygen to form a nitro-containing reaction product; hydrogenating the nitro-containing reaction product; and then recovering the organic nitrogen compound.

15. The process of claim 14 in which a polymer of a $C_3$–$C_6$-olefin is used.

16. The process of claim 14 in which the $C_3$–$C_6$-olefin is selected from the group consisting of propene, 1-butene, 2-butene and isobutene.

* * * * *